(12) United States Patent
Nosaka et al.

(10) Patent No.: US 11,126,084 B2
(45) Date of Patent: Sep. 21, 2021

(54) COMPOSITION FOR RESIST UNDERLAYER FILM FORMATION, RESIST UNDERLAYER FILM AND FORMING METHOD THEREOF, PRODUCTION METHOD OF PATTERNED SUBSTRATE, AND COMPOUND

(71) Applicant: JSR CORPORATION, Tokyo (JP)

(72) Inventors: Naoya Nosaka, Tokyo (JP); Goji Wakamatsu, Tokyo (JP); Tsubasa Abe, Tokyo (JP); Yuushi Matsumura, Tokyo (JP); Yoshio Takimoto, Tokyo (JP); Shin-ya Nakafuji, Tokyo (JP); Kazunori Sakai, Tokyo (JP)

(73) Assignee: JSR CORPORATION, Tokyo (JP)

( * ) Notice: Subject to any disclaimer, the term of this patent is extended or adjusted under 35 U.S.C. 154(b) by 279 days.

(21) Appl. No.: 16/388,238

(22) Filed: Apr. 18, 2019

(65) Prior Publication Data
US 2019/0243247 A1    Aug. 8, 2019

Related U.S. Application Data

(63) Continuation of application No. PCT/JP2017/037766, filed on Oct. 18, 2017.

(30) Foreign Application Priority Data

Oct. 20, 2016   (JP) .............................. JP2016-206417

(51) Int. Cl.
| | |
|---|---|
| *G03F 7/11* | (2006.01) |
| *C08G 61/02* | (2006.01) |
| *C09D 165/00* | (2006.01) |
| *G03F 7/16* | (2006.01) |
| *G03F 7/20* | (2006.01) |
| *G03F 7/26* | (2006.01) |
| *C07C 35/37* | (2006.01) |
| *C07C 33/28* | (2006.01) |
| *C07C 35/44* | (2006.01) |
| *C07C 43/166* | (2006.01) |
| *H01L 21/027* | (2006.01) |

(Continued)

(52) U.S. Cl.
CPC .............. *G03F 7/11* (2013.01); *C07C 33/28* (2013.01); *C07C 35/37* (2013.01); *C07C 35/44* (2013.01); *C07C 43/166* (2013.01); *C08F 299/02* (2013.01); *C08G 61/02* (2013.01); *C09D 165/00* (2013.01); *G03F 7/162* (2013.01); *G03F 7/168* (2013.01); *G03F 7/20* (2013.01); *G03F 7/26* (2013.01); *H01L 21/027* (2013.01); *H01L 21/0273* (2013.01); *H01L 21/3081* (2013.01); *C07C 2602/42* (2017.05); *C07C 2603/20* (2017.05); *C07C 2603/50* (2017.05); *C07C 2603/54* (2017.05); *C08G 2261/148* (2013.01); *C08G 2261/1414* (2013.01); *C08G 2261/1422* (2013.01); *C08G 2261/1424* (2013.01); *H01L 21/3065* (2013.01)

(58) Field of Classification Search
CPC ............ H01L 21/3081; H01L 21/3065; H01L 21/027; H01L 21/0273; C08G 61/02; C08G 2261/1422; C08G 2261/1424; C08G 2261/1414; C08G 2261/148; C08G 2261/76; C08G 2261/3424; C08G 2261/135; C08G 2261/42; C08G 8/12; C08G 10/00; C08G 2261/1412; C07C 2603/20; C07C 2603/54; C07C 2603/50; C07C 2602/42; C07C 35/37; C07C 33/28; C07C 35/44; C07C 43/166; G03F 7/094; G03F 7/11; G03F 7/162; G03F 7/168; G03F 7/20; G03F 7/26; C08F 299/02; C09D 165/00
USPC .................................. 430/270.1, 271.1, 311
See application file for complete search history.

(56) References Cited

U.S. PATENT DOCUMENTS

| | | |
|---|---|---|
| 2015/0185613 A1 | 7/2015 | Toyokawa et al. |
| 2016/0259247 A1 | 9/2016 | Toyokawa et al. |

(Continued)

FOREIGN PATENT DOCUMENTS

| | | |
|---|---|---|
| CN | 102695986 A | 9/2012 |
| JP | 5-238990 A | 9/1993 |

(Continued)

OTHER PUBLICATIONS

International Search Report dated Jan. 23, 2018 in PCT/JP2017/037766, 11 pages.

(Continued)

*Primary Examiner* — Caleen O Sullivan
(74) *Attorney, Agent, or Firm* — Element IP, PLC

(57) ABSTRACT

A composition for resist underlayer film formation contains a compound having a group represented by formula (1), and a solvent. $R^1$ represents an organic group having 2 to 10 carbon atoms and having a valency of (m+n), wherein the carbon atoms include two carbon atoms that are adjacent to each other, with a hydroxy group or an alkoxy group bonding to one of the two carbon atoms, and with a hydrogen atom bonding to another of the two carbon atoms; $L^1$ represents an ethynediyl group or a substituted or unsubstituted ethenediyl group; $R^2$ represents a hydrogen atom or a monovalent organic group having 1 to 20 carbon atoms; n is an integer of 1 to 3; * denotes a bonding site to a moiety other than the group represented by the formula (1) in the compound; and m is an integer of 1 to 3.

(Continued)

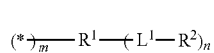

19 Claims, 1 Drawing Sheet

(51) Int. Cl.
*H01L 21/308* (2006.01)
*C08F 299/02* (2006.01)
*H01L 21/3065* (2006.01)

(56) References Cited

U.S. PATENT DOCUMENTS

2016/0347965 A1 12/2016 Umezaki et al.
2019/0079397 A1 3/2019 Endo et al.

FOREIGN PATENT DOCUMENTS

| JP | 2004-177668 A | 6/2004 |
| JP | 2017-151389 A | 8/2017 |
| WO | WO 2014/038680 A1 | 3/2014 |
| WO | WO 2015/122296 A1 | 8/2015 |
| WO | WO 2017/154921 A1 | 9/2017 |

OTHER PUBLICATIONS

Written Opinion of the International Searching Authority dated Jan. 23, 2018 in PCT/JP2017/037766 filed Oct. 18, 2017, (with English translation ), 17 pages.
Qun-Sheng Guo, et al., "A Facile Synthesis of 3 or 3,3'-Substituted Binaphthols and their Applications in the Asymmetric Addition of Diethylzinc to Aldehydes" Journal of Organometallic Chemistry, 2006, vol. 691, No. 6, pp. 1282-1287.
Yasmeen Badar, et. al., "Optical Activity in the 1,1'-Binaphthyl Series. Optically Active 8,8'-Dimethyl-1,1'-Binaphthyl" Journal of the Chemical Society, 1965, pp. 1412-1418.
Jen-Chieh Hsieh, et al., "O-Dihaloarenes as Aryne Precursors for Nickel-Catalyzed [2 + 2 + 2] Cycloaddition with Alkynes and Nitriles" Chemical Communications, No. 26, 2008, pp. 2992-2994.
R. G. R. Bacon, et al., "Cyclisations with Hydrazine Part III.[1] Syntheses of Pentaphene and Dinaphtho[2,1-d: 1',2' f] [1,2] Diazocine" Journal of the Chemical Society, 1963, pp. 839-845.
Katsuhisa Mizoguchi, et al., "Negative-Working Photosensitive Poly(Phenylene Ether) Based on Poly(2,6-Dimethyl-1,4-Phenylene Ether), a Cross-Linker, and a Photoacid Generator" Macromolecules, vol. 43, 2010, pp. 2832-2839.
Katsuhisa Mizoguchi, et al., "Direct Patterning of Poly(Ether Ether Sulfone) Using a Cross-Linker and a Photoacid Generator" Polymer Journal, vol. 40, No. 7, 2008, pp. 645-650.
Katsuhisa Mizoguchi, et al., "Negative-Type Photosensitive Poly(Phenylene Ether) Based on Poly(2,6-Dimethyl-1,4-Phenylene Ether), a Crosslinker, and a Photoacid Generator" Journal of Polymer Science: Part A, Polymer Chemistry, vol. 46, 2008, pp. 4949-4958.
Office Action dated Jul. 20, 2021 in Japanese Patent Application No. 2018-546392 (with English translation), 10 pages.
Combined Office Action and Search Report dated Mar. 3, 2021 in Taiwanese Patent Application No. 106135861 (with English translation), 21 pages.

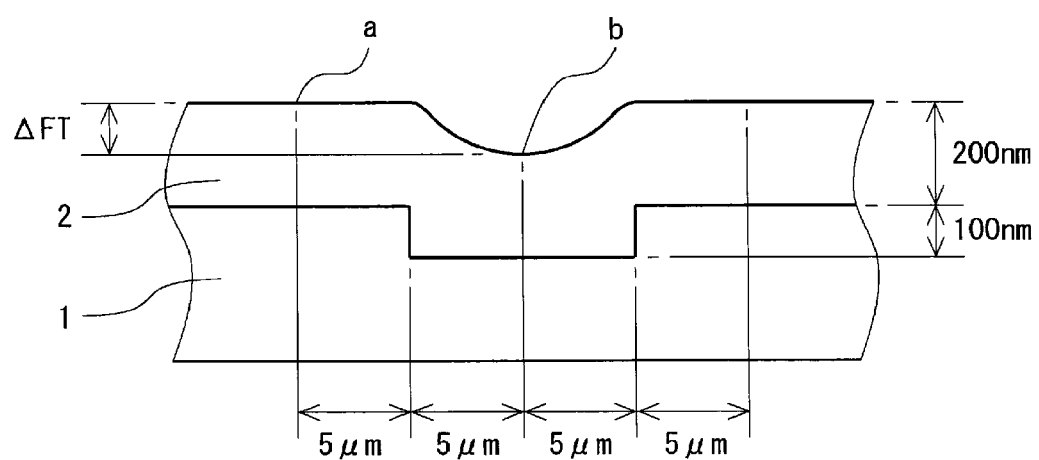

COMPOSITION FOR RESIST UNDERLAYER FILM FORMATION, RESIST UNDERLAYER FILM AND FORMING METHOD THEREOF, PRODUCTION METHOD OF PATTERNED SUBSTRATE, AND COMPOUND

CROSS-REFERENCE TO RELATED APPLICATIONS

The present application is a continuation application of International Application No. PCT/JP2017/037766, filed Oct. 18, 2017, which claims priority to Japanese Patent Application No. 2016-206417, filed Oct. 20, 2016. The contents of these applications are incorporated herein by reference in their entirety.

BACKGROUND OF THE INVENTION

Field of the Invention

The present invention relates to a composition for resist underlayer film formation, a resist underlayer film and a method for forming the same, a production method of a patterned substrate, and a compound.

Description of the Related Art

In manufacturing semiconductor devices, multilayer resist processes have been employed for attaining a high degree of integration. In these processes, a composition for film formation is first applied directly or indirectly on a substrate, and then a film thus obtained is heated, thereby forming a resist underlayer film. A resist pattern is formed by using a resist composition directly or indirectly on the resist underlayer film. Subsequently, the resist underlayer film is etched by using the resist pattern as a mask, and the substrate is further etched by using the resultant resist underlayer film pattern as a mask, thereby enabling a desired pattern to be formed on the substrate. Accordingly, a patterned substrate can be obtained. The resist underlayer film for use in such a multilayer resist process is required to have superior coating characteristics and superior etching resistance.

Recently, there are increasing cases of pattern formation on a substrate having multiple types of trenches, particularly trenches with aspect ratios that are different from one another. In these cases, the composition for resist underlayer film formation used for forming a resist underlayer film is required to sufficiently fill these trenches, and to provide superior flatness.

Moreover, the multilayer resist processes involving a procedure of forming a hard mask as an intermediate layer on the resist underlayer film has been contemplated recently. Specifically, since an inorganic hard mask is formed on a resist underlayer film using CVD techniques according to this procedure, particularly in a case where a nitride inorganic hard mask is formed, the temperature is elevated to be as high as at least 300° C. and typically no less than 400° C., and thus, the resist underlayer film is required to have superior heat resistance. In the case of having insufficient heat resistance, a component in the resist underlayer film may be sublimated and the sublimated component may adhere to the substrate again, resulting in a disadvantage of a decrease in yields of the production of semiconductor devices.

To meet these demands, structures of polymers, etc. contained in the composition for resist underlayer film formation, and functional groups included in the polymers have been extensively investigated (see Japanese Unexamined Patent Application, Publication No. 2004-177668).

SUMMARY OF THE INVENTION

According to an aspect of the present invention, a composition for resist underlayer film formation includes a compound comprising a group represented by formula (1); and a solvent.

In the formula (1), $R^1$ represents an organic group having 2 to 10 carbon atoms and having a valency of (m+n), wherein the carbon atoms include two carbon atoms that are adjacent to each other, with a hydroxy group or an alkoxy group bonding to one of the two carbon atoms, and with a hydrogen atom bonding to another of the two carbon atoms; $L^1$ represents an ethynediyl group or a substituted or unsubstituted ethenediyl group; $R^2$ represents a hydrogen atom or a monovalent organic group having 1 to 20 carbon atoms; n is an integer of 1 to 3, wherein in a case where n is no less than 2, a plurality of $L^1$s are identical or different, and a plurality of $R^2$s are identical or different; * denotes a bonding site to a moiety other than the group represented by the formula (1) in the compound; and m is an integer of 1 to 3.

According to another aspect of the present invention, a resist underlayer film is formed from the composition.

According to further aspect of the present invention, a method for resist underlayer film formation includes: applying the composition directly or indirectly on an upper face side of a substrate to form a coating film; and heating the coating film.

According to further aspect of the present invention, a production method of a patterned substrate includes: forming a resist pattern directly or indirectly on an upper face side of the resist underlayer film; and carrying out etching using the resist pattern as a mask.

According to further aspect of the present invention, a compound includes a group represented by formula (1).

In the formula (1), $R^1$ represents an organic group having 2 to 10 carbon atoms and having a valency of (m+n), wherein the carbon atoms comprise two carbon atoms that are adjacent to each other, with a hydroxy group or an alkoxy group bonding to one of the two carbon atoms, and with a hydrogen atom bonding to another of the two carbon atoms; $L^1$ represents an ethynediyl group or a substituted or unsubstituted ethenediyl group; $R^2$ represents a hydrogen atom or a monovalent organic group having 1 to 20 carbon atoms; n is an integer of 1 to 3, wherein in a case where n is no less than 2, a plurality of $L^1$s are identical or different, and a plurality of $R^2$s are identical or different; * denotes a bonding site to a moiety other than the group represented by the formula (1) in the compound; and m is an integer of 1 to 3.

BRIEF DESCRIPTION OF THE DRAWINGS

The FIGURE is a schematic cross sectional view for illustrating an evaluation method of flatness.

DESCRIPTION OF THE EMBODIMENTS

According to one embodiment of the invention, a composition for resist underlayer film formation contains a compound having a group represented by the following formula (1) (hereinafter, may be also referred to as "(A) compound" or "compound (A)"), and a solvent (hereinafter, may be also referred to as "(B) solvent" of "solvent (B)").

(1)

wherein, in the formula (1), $R^1$ represents an organic group having 2 to 10 carbon atoms and having a valency of (m+n), wherein the carbon atoms include two carbon atoms that are adjacent to each other, with a hydroxy group or an alkoxy group bonding to one of the two carbon atoms, and with a hydrogen atom bonding to another of the two carbon atoms; $L^1$ represents an ethynediyl group or a substituted or unsubstituted ethenediyl group; $R^2$ represents a hydrogen atom or a monovalent organic group having 1 to 20 carbon atoms; n is an integer of 1 to 3, wherein in a case where n is no less than 2, a plurality of $L^1$s may be identical or different, and a plurality of $R^2$s may be identical or different; * denotes a bonding site to a moiety other than the group represented by the above formula (1) in the compound (A); and m is an integer of 1 to 3.

According to another embodiment of the invention, a resist underlayer film is formed from the composition for resist underlayer film formation according to the one embodiment.

According to still another embodiment of the invention, a method for resist underlayer film formation includes: applying the composition for resist underlayer film formation according to the one embodiment, directly or indirectly on an upper face side of a substrate; and heating a coating film obtained by the applying of the composition.

According to yet another embodiment of the invention, a production method of a patterned substrate includes:
forming a resist pattern directly or indirectly on an upper face side of the resist underlayer film obtained by the method for resist underlayer film formation according to the still another embodiment of the invention; and carrying out etching using the resist pattern as a mask.

According to yet still another embodiment of the invention, a compound includes the group represented by the above formula (1).

The composition for resist underlayer film formation according to the one embodiment of the present invention enables a resist underlayer film that is superior in etching resistance, flatness and heat resistance to be formed with superior coating characteristics being exhibited. The resist underlayer film according to the another embodiment of the present invention is superior in etching resistance, flatness and heat resistance. The method for resist underlayer film formation according to the still another embodiment of the present invention is capable of forming a resist underlayer film that is superior in etching resistance, flatness and heat resistance, with superior coating characteristics being exhibited. The production method of a patterned substrate according to the yet another embodiment of the present invention enables a substrate having a favorable pattern configuration to be obtained by using the superior resist underlayer film formed. The compound according to the yet still another embodiment of the present invention can be suitably used as a component of the composition for resist underlayer film formation according to the one embodiment of the present invention. Therefore, these can be suitably used for manufacture, etc., of semiconductor devices in which further progress of microfabrication is expected in the future. Hereinafter, the embodiments of the present invention will be described in detail.

Composition for Resist Underlayer Film Formation

The composition for resist underlayer film formation of the one embodiment of the invention contains the compound (A) and the solvent (B). The composition for resist underlayer film formation may contain as a favorable component, an acid generating agent (hereinafter, may be also referred to as "(C) acid generating agent" or "acid generating agent (C)") and/or a crosslinking agent (hereinafter, may be also referred to as "(D) crosslinking agent" or "crosslinking agent (D)"), and may further contain other optional component within a range not leading to impairment of the effects of the present invention. Hereinafter, each component is explained.

(A) Compound

The compound (A) has a group represented by the following formula (1) (hereinafter, may be also referred to as "group (I)"). The compound (A) may have one group (I), or two or more groups (I). One, or two or more types of the compound (A) may be contained.

(1)

In the above formula (1), $R^1$ represents an organic group having 2 to 10 carbon atoms and having a valency of (m+n), wherein the carbon atoms include two carbon atoms that are adjacent to each other, with a hydroxy group or an alkoxy group bonding to one of the two carbon atoms, and with a hydrogen atom bonding to another of the two carbon atoms; $L^1$ represents an ethynediyl group or a substituted or unsubstituted ethenediyl group; $R^2$ represents a hydrogen atom or a monovalent organic group having 1 to 20 carbon atoms; n is an integer of 1 to 3, wherein in a case where n is no less than 2, a plurality of $L^1$s may be identical or different, and a plurality of $R^2$s may be identical or different; * denotes a bonding site to a moiety other than the group represented by the formula (1) in the compound; and m is an integer of 1 to 3.

Due to the compound (A) having the group (I), the composition for resist underlayer film formation enables a resist underlayer film that is superior in etching resistance, flatness and heat resistance to be formed, with superior coating characteristics being exhibited. Although not necessarily clarified and without wishing to be bound by any theory, the reason for the aforementioned effects achieved by the composition for resist underlayer film formation due to the constitution described above can be inferred as in the following, for example. Specifically, owing to having a hydroxy group or an alkoxy group in $R^1$ of the group (I) in the compound (A), the composition for resist underlayer film formation is capable of exhibiting superior coating characteristics, and improving the flatness. Moreover, $R^1$ has a structure including two carbon atoms that are adjacent to each other, with a hydroxy group or an alkoxy group bonding to one of the two carbon atoms, and with a hydrogen atom bonding to another of the two carbon atoms; therefore, heating would result in a dehydration reaction or a dealcoholization reaction (hereinafter, may be also referred to as "dehydration reaction, etc.") in which the hydroxy group or the alkoxy group is detached, whereby a carbon-carbon double bond is produced and a content of oxygen atoms decreases. Consequently, it is considered that the etching resistance would be improved through an increased content of carbon atoms. Furthermore, the carbon-carbon double bond thus produced and a carbon-carbon multiple bond in the ethynediyl group or the ethanediyl group represented by $L^1$ are capable of forming a highly dense cross-linked structure through heating, and as a result, the etching resistance and the heat resistance are considered to be improved.

The organic group having 2 to 10 carbon atoms and having a valency of (m+n) represented by $R^1$ is exemplified by: a hydrocarbon group having 2 to 10 carbon atoms and a valency of (m+n), and having two carbon atoms that are adjacent to each other; a group (α) having a divalent hetero atom-containing group between two adjacent carbon atoms of this hydrocarbon group; a group obtained by substituting with a monovalent hetero atom-containing group, a part of hydrogen atoms of the hydrocarbon group or the group (α) to give a group (β), and then substituting with a hydroxy group or an alkoxy group, one of hydrogen atoms bonding to the two carbon atoms included in the hydrocarbon group, the group (α) or the group (β); and the like.

Examples of the alkoxy group include a methoxy group, an ethoxy group, a propoxy group, a butoxy group, a pentyloxy group, and the like.

Examples of the hydrocarbon group having 2 to 10 carbon atoms having a valency of (m+n) include groups obtained by removing (m+n) hydrogen atoms from a hydrocarbon exemplified by alicyclic saturated hydrocarbons such as hydrocarbons having 1 to 10 carbon atoms chain, e.g.,
alkanes such as ethane, propane and butane;
alkenes such as ethene, propene and butene; and
alkynes such as ethyne, propyne and butyne,
alicyclic hydrocarbons having 3 to 10 carbon atoms involving
alicyclic saturated hydrocarbons, e.g.,
cycloalkanes such as cyclopentane and cyclohexane; and
bridged cyclic saturated hydrocarbons such as norbornane, adamantane and tricyclodecane,
alicyclic unsaturated hydrocarbons, e.g.,
cycloalkenes such as cyclopentene and cyclohexene; and
bridged cyclic unsaturated hydrocarbons such as norbornane and tricyclodecane
aromatic hydrocarbons having 6 to 10 carbon atoms, e.g.,
arenes such as benzene, toluene, xylene and naphthalene, and the like.

The hetero atom constituting the monovalent or divalent hetero atom-containing group is exemplified by an oxygen atom, a nitrogen atom, a sulfur atom, a phosphorus atom, a silicon atom, a halogen atom, and the like. Examples of the halogen atom include a fluorine atom, a chlorine atom, a bromine atom, an iodine atom, and the like.

The divalent hetero atom-containing group is exemplified by —O—, —CO—, —S—, —CS—, —NR'—, a group obtained by combining two or more of these, or the like, wherein R' represents a hydrogen atom or a monovalent hydrocarbon group.

Examples of the monovalent hetero atom-containing group include halogen atoms such as a fluorine atom, a chlorine atom, a bromine atom and an iodine atom, a carboxy group, a cyano group, an amino group, a sulfanyl group, and the like.

It is preferred that in a case in which (m+n) in the above formula (1) is no greater than 4, $R^1$ includes a structure represented by the following formula (A) (hereinafter, may be also referred to as "structure (A)"). The two carbon atoms that are adjacent to each other in the structure (A), with a hydroxy group or an alkoxy group bonding to one of the two carbon atoms, and with a hydrogen atom bonding to another of the two carbon atoms are adjacent to the ethynediyl group or the ethenediyl group represented by $L^1$. Due to the compound (A) having such a structure (A), a dehydration reaction, etc., more readily proceeds in the composition for resist underlayer film formation, thereby consequently enabling etching resistance and heat resistance to be more improved.

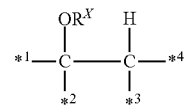

(A)

In the above formula (A), $R^X$ represents a hydrogen atom or an alkyl group having 1 to 8 carbon atoms; n bonding sites among *1 to *4 represent bonding sites to $L^1$ in the above formula (1), whereas m bonding sites among *1 to *4 represent bonding sites to a moiety other than the group (I) in the compound (A). In a case in which (m+n) is 2 or 3, a hydrogen atom or a monovalent organic group bonds to (4−m−n) bonding sites among *1 to *4.

In the structure (A), an organic group is preferably bonded to *1 and *2. In other words, it is preferred that a hydrogen atom does not bond to the carbon atom to which the hydroxy group and the alkoxy group of the organic group in $R^1$ bond. The organic group boned to *1 and *2 is preferably a hydrocarbon group, and more preferably an aromatic hydrocarbon group. Alternatively, an aromatic ring is preferably bonded to at least any one of *1 and *2. The aromatic ring is exemplified by a benzene ring, a naphthalene ring, an anthracene ring, a pyrene ring, and the like. Such a structure enables the etching resistance and heat resistance to be more improved. It is to be noted that in a case in which the organic group bonds to both *1 and *2, these organic groups may form a ring structure together with the carbon atom to which these organic groups bond.

$R^X$ represents preferably a hydrogen atom, a methyl group or an ethyl group, more preferably a hydrogen atom or a methyl group, and still more preferably a hydrogen atom. When $R^X$ represents the group described above, the dehydration reaction, etc. more readily proceeds in the composition for resist underlayer film formation, thereby consequently enabling the etching resistance and heat resistance to be more improved.

The substituent of the ethenediyl group represented by $L^1$ is exemplified by a monovalent organic group having 1 to 10 carbon atoms and the like, preferably a hydrocarbon group, and more preferably an alkyl group.

$L^1$ represents preferably an ethynediyl group or an unsubstituted ethenediyl group.

The monovalent organic group having 1 to 20 carbon atoms which may be represented by $R^2$ is exemplified by: a monovalent hydrocarbon group having 1 to 20 carbon atoms; a group (α) that includes a divalent hetero atom-containing group between two adjacent carbon atoms of the hydrocarbon group having 1 to 20 carbon atoms; a group obtained from the hydrocarbon group having 1 to 20 carbon atoms or the group (α) by substituting a part or all of hydrogen atoms included therein with a monovalent hetero atom-containing group; and the like.

In light of improvements of the etching resistance and heat resistance, $R^2$ represents preferably a hydrogen atom or a hydrocarbon group, more preferably a hydrogen atom or an alkyl group, still more preferably a hydrogen atom or a methyl group, and particularly preferably a hydrogen atom.

It is preferred that n is 1 or 2, and 1 is more preferred.

It is preferred that m is 1 or 2, and 1 is more preferred.

The group (I) is preferably a group represented by the following formula (1-1) or (1-2) (hereinafter, may be also referred to as "group (I-1) or (I-2)"). The groups (I-1) and (I-2) are candidates of the group (I), wherein $R^1$ has two carbon atoms; n is 1; and m is 2 or 3.

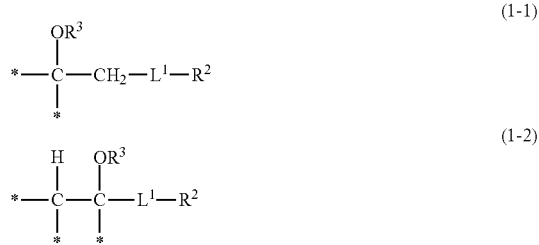

In the above formulae (1-1) and (1-2), $R^3$s each independently represent a hydrogen atom or an alkyl group having 1 to 8 carbon atoms; and $L^1$, $R^2$ and * are as defined in the above formula (1).

$R^3$ represents preferably a hydrogen atom, a methyl group or an ethyl group, more preferably a hydrogen atom or a methyl group, and still more preferably a hydrogen atom.

The structure of the moiety to which the group (I) bonds in the compound (A) is exemplified by an organic group having 1 to 50 carbon atoms, and the like.

The group (I) in the compound (A) may be formed by, for example: allowing a compound having a carbonyl group to react with a Grignard reagent having a carbon-carbon double bond such as allylmagnesium chloride in a solvent such as tetrahydrofuran; or converting a hydroxy group of this product into an alkoxy group by allowing to react with an alkyl halide such as methyl iodide in the presence of a base such as sodium hydride in a solvent such as tetrahydrofuran. Alternatively, the group (I) may be formed by, for example, allowing a compound having a carbonyl group to react with a halide having a carbon-carbon triple bond such as propargyl bromide in the presence of a base such as n-butyllithium/tetramethylethylenediamine in a solvent such as cyclohexane. The compound (A) can be thus synthesized conveniently from a ketone compound.

The lower limit of the number of the group (I) included in the compound (A) is preferably 2, and more preferably 3. The upper limit of the number of the group (I) is preferably 20, more preferably 10, and still more preferably 4. When the number of the group (I) in the compound (A) falls within the above range, the etching resistance, flatness and heat resistance can be more improved.

The upper limit of the content of oxygen atoms in the compound (A) is preferably 3% by mass, more preferably 4% by mass, still more preferably 5% by mass, and particularly preferably 6% by mass. The upper limit of the content of oxygen atoms is preferably 15% by mass, more preferably 12% by mass, still more preferably 10% by mass, and particularly preferably 9% by mass. When the content of oxygen atoms in the compound (A) falls within the above range, the composition for resist underlayer film formation can have etching resistance, flatness and heat resistance being more improved. The content of oxygen atoms in the compound (A) may be determined by analyzing the structure of the compound (A), and calculating the content from the structure thus analyzed.

The compound (A) preferably has an aromatic ring. Due to the compound (A) having an aromatic ring, the composition for resist underlayer film formation enables the etching resistance and heat resistance to be more improved. The aromatic ring is exemplified by a benzene ring, a naphthalene ring, an anthracene ring, a pyrene ring, and the like. The aromatic ring in the compound (A) preferably bonds to at least any of two bonding sites in the above formula (1-1), or to at least any of three bonding sites in the above formula (1-2).

The compound (A) is exemplified by an aromatic ring-containing compound having a molecular weight of no less than 300 and no greater than 3,000 (hereinafter, may be also referred to as "aromatic ring-containing compound (I)"), a resin (hereinafter, may be also referred to as "resin (I)"), and the like. The "resin" as referred to herein means a polymer. The "aromatic ring-containing compound" as referred to herein means a compound having an aromatic ring and being other than a polymer. Hereinafter, descriptions are presented in the order of the aromatic ring-containing compound (I) and the resin (I).

Aromatic Ring-Containing Compound (I)

The aromatic ring-containing compound (I) is a compound that includes the group (I) and an aromatic ring, and that has a molecular weight of no less than 300 and no greater than 3,000. In the case of aromatic ring-containing compound (I) being accompanied by molecular weight distribution, the molecular weight of the aromatic ring-containing compound (I) may be, for example, polystyrene equivalent weight average molecular weight (Mw) as determined by gel permeation chromatography (GPC).

The aromatic ring-containing compound (I) is exemplified by a compound represented by the following formula (i), and the like.

In the above formula (i), Z represents the group (I) wherein m is 2; $Ar^1$ represents a group obtained by removing k hydrogen atoms on the aromatic ring in a substituted or unsubstituted aromatic hydrocarbon having 6 to 50 carbon atoms; $Ar^2$ represents a substituted or unsubstituted aryl group having 6 to 50 carbon atoms; k is an integer of 1 to 10, wherein in a case where k is no less than 2, a plurality of Zs may be identical or different, and a plurality of $Ar^2$s may be identical or different; and $Ar^1$ and one or a plurality of $Ar^2$s may bond with each other.

Examples of the aromatic hydrocarbon having 6 to 50 carbon atoms that gives the group represented by $Ar^1$ include benzene, naphthalene, anthracene, phenanthrene, pyrene, tetracene, chrysene, pentacene, hexacene, coronene, trinaphthylene, heptacene, ovalene, pentalene, indene, azulene, heptalene, biphenylene, indacene, acenaphthylene, fluorene, phenalene, aceanthrylene, perylene, picene, tetraphenylene, hexaphene, rubicene, trinaphthylene, heptaphene, pyranthrene, hexahelicene, and the like. Of these, benzene, pyrene and coronene are preferred.

Exemplary aryl group represented by $Ar^2$ may include groups obtained by removing one hydrogen atom on the aromatic ring from the aromatic hydrocarbon that gives $Ar^1$ exemplified above, and the like. Of these, a phenyl group, a naphthyl group and a pyrenyl group are preferred.

The substituent of the aromatic hydrocarbon group is exemplified by a hydroxy group, a halogen atom, an alkoxy group, a nitro group, a cyano group, a carboxy group, and the like. In light of the etching resistance and heat resistance, it is preferred that the aromatic hydrocarbon group does not have a substituent. It is to be noted that the substituent of the aromatic hydrocarbon group may be the group (I).

The lower limit of k is preferably 2, and more preferably 3. The upper limit of k is preferably 6, and more preferably 4.

The lower limit of the molecular weight of the aromatic ring-containing compound (I) is preferably 350, and more preferably 400. The upper limit of the molecular weight of the aromatic ring-containing compound (I) is preferably 2,000, more preferably 1,000, and still more preferably 800. When the molecular weight of the aromatic ring-containing compound (I) falls within the above range, the composition for resist underlayer film formation can provide more improved flatness.

Resin (I)

The resin (I) has the group (I). The resin (I) is exemplified by a resin having an aromatic ring in the main chain thereof, a resin not having an aromatic ring in the main chain thereof but having the aromatic ring in the side chain thereof, and the like. The term "main chain" as referred to means the longest one of the chains constituted of atoms in the compound (A). The term "side chain" as referred to means a chain constituted of atoms in the compound (A) other than the longest one. The resin (I) is typically a compound including a plurality of the groups (I).

The resin (I) may be synthesized according to a procedure described in paragraph [0041] by using as a source material, a resin having an aromatic ring to which a group including a carbonyl group such as a formyl group bonds, for example.

The lower limit of the Mw of the resin (I) is preferably 500 and more preferably 1,000. Meanwhile, the upper limit of Mw is preferably 50,000, more preferably 10,000, and still more preferably 8,000.

The lower limit of the Mw/Mn of the resin (I) is typically 1, and preferably 1.1. The upper limit of the Mw/Mn is preferably 5, more preferably 3, and still more preferably 2.

When the Mw and the Mw/Mn of the resin (I) fall within the above ranges, more improvements of the flatness and surface coating characteristics which may be provided by the composition for resist underlayer film formation are enabled.

Examples of the compound (A) include: the aromatic ring-containing compounds (I) such as compounds represented by the following formulae (i-1) to (i-4); the resins (I) such as resins having a structural unit represented by the following formula (p-1) or (p-2); and the like. A linkage —$Ar^{1'}$—$Z^1$—$Ar^{1'}$— in the following formula (i-4) corresponds to a group obtained by removing two hydrogen atoms on the aromatic ring of the aromatic hydrocarbon having 6 to 50 carbon atoms having $Ar^1$ been substituted in the above formula (i).

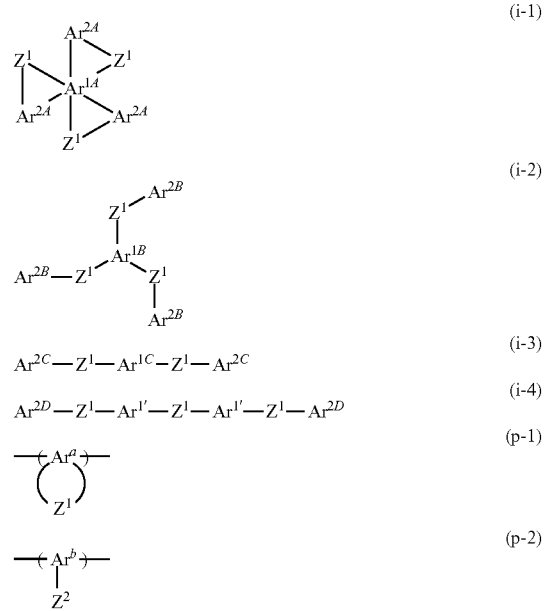

In the above formulae (i-1) to (i-4) and (p-1), $Z^1$s each independently represent the group (I), wherein m is 2, and $R^1$ is represented by the above formula (1-1).

In the above formula (p-2), $Z^2$ represents the group (I), wherein m is 1, and $R^1$ is represented by the above formula (1-1).

In the above formula (i-1), $Ar^{1A}$ represents a group obtained by removing six hydrogen atoms on the aromatic ring of the substituted or unsubstituted aromatic hydrocarbon having 6 to 50 carbon atoms; and $Ar^{2A}$s each independently represent a group obtained by removing two hydrogen atoms on the aromatic ring of the substituted or unsubstituted aromatic hydrocarbon having 6 to 50 carbon atoms. $Ar^{1A}$ represents preferably a benzenehexayl group. $Ar^{2A}$ represents preferably a benzenediyl group.

In the above formula (i-2), $Ar^{1B}$ represents a group obtained by removing three hydrogen atoms on the aromatic ring of the substituted or unsubstituted aromatic hydrocarbon having 6 to 50 carbon atoms; and $Ar^{2B}$s each independently represent a substituted or unsubstituted aryl group having 6 to 50 carbon atoms. $Ar^{1B}$ represents preferably a benzenetriyl group. $Ar^{2B}$ represents preferably a naphthyl group.

In the above formula (i-3), $Ar^{1C}$ represents a group obtained by removing two hydrogen atoms on the aromatic ring of the substituted or unsubstituted aromatic hydrocarbon having 6 to 50 carbon atoms; and $Ar^{2C}$s each independently represent a substituted or unsubstituted aryl group having 6 to 50 carbon atoms. $Ar^{1C}$ represents preferably a benzenediyl group or a coronenediyl group. $Ar^{2C}$ represents preferably a phenyl group, a naphthyl group or a pyrenyl group.

In the above formula (i-4), $Ar^{1'}$s each independently represent a group obtained by removing two hydrogen atoms on the aromatic ring of the substituted or unsubstituted aromatic hydrocarbon having 6 to 20 carbon atoms; and $Ar^{2D}$s each independently represent a substituted or unsubstituted aryl group having 6 to 50 carbon atoms. $Ar^{1'}$ represents preferably a pyrenediyl group. $Ar^{2D}$ represents preferably a phenyl group.

In the above formula (p-1), $Ar^a$ represents a structure obtained by removing four hydrogen atoms from the substituted or unsubstituted aromatic hydrocarbon having 6 to 50 carbon atoms. $Ar^a$ represents preferably a structure obtained by removing four hydrogen atoms from acenaphthen-yl-biphenyl.

In the above formula (p-2), $Ar^b$ represents a structure obtained by removing three hydrogen atoms from the substituted or unsubstituted aromatic hydrocarbon having 6 to 50 carbon atoms. $Ar^b$ represents preferably a structure obtained by removing three hydrogen atoms from acenaphthene.

The lower limit of the content of the compound (A) with respect to the total solid content in the composition for resist underlayer film formation is preferably 70% by mass, more preferably 80% by mass, and still more preferably 85% by mass. Meanwhile, the upper limit of the content is, for example, 100% by mass. The "total solid content" as referred to means the sum of the components other than the solvent (B) in the composition for resist underlayer film formation.

The lower limit of the content of the compound (A) in the composition for resist underlayer film formation is preferably 1% by mass, more preferably 3% by mass, and still more preferably 5% by mass. The upper limit of the content is preferably 50% by mass, more preferably 30% by mass, and still more preferably 15% by mass.

(B) Solvent

The solvent (B) is not particularly limited as long as it can dissolve or disperse the compound (A), and the optional component contained as needed.

The solvent (B) is exemplified by an alcohol solvent, a ketone solvent, an ether solvent, an ester solvent, a nitrogen-containing solvent, and the like. The solvent (B) may be used either alone of one type, or in combination of two or more types thereof.

Examples of the alcohol solvent include: monoalcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenyl methyl carbinol, diacetone alcohol and cresol; polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin; and the like.

Examples of the ketone solvent include acetone, methyl ethyl ketone, methyl n-propyl ketone, methyl n-butyl ketone, diethyl ketone, methyl iso-butyl ketone, methyl-n-pentyl ketone, ethyl n-butyl ketone, methyl n-hexyl ketone, di-iso-butyl ketone, trimethylnonanone, cyclohexanone, methylcyclohexanone, 2,4-pentanedione, acetonylacetone, diacetone alcohol, acetophenone, fenchone, and the like.

Examples of the ether solvent include ethyl ether, iso-propyl ether, n-butyl ether, n-hexyl ether, 2-ethyl hexyl ether, ethylene oxide, 1,2-propylene oxide, dioxolane, 4-methyl dioxolane, dioxane, dimethyl dioxane, 2-methoxyethanol, 2-ethoxyethanol, ethylene glycol diethyl ether, 2-n-butoxyethanol, 2-n-hexoxyethanol, 2-phenoxyethanol, 2-(2-ethylbutoxy)ethanol, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, 1-n-butoxy-2-propanol, 1-phenoxy-2-propanol, propylene glycol monomethyl ether, propylene glycol monoethyl ether, propylene glycol monopropyl ether, dipropylene glycol monomethyl ether, dipropylene glycol monoethyl ether, dipropylene glycol monopropyl ether, tripropylene glycol monomethyl ether, tetrahydrofuran, 2-methyltetrahydrofuran, and the like.

Examples of the ester solvent include diethyl carbonate, methyl acetate, ethyl acetate, γ-butyrolactone, γ-valerolactone, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methyl cyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the nitrogen-containing solvent include N-methylformamide, N,N-dimethylformamide, N,N-diethylformamide, acetamide, N-methylacetamide, N,N-dimethylacetamide, N-methylpropionamide, N-methylpyrrolidone, and the like.

Of these, the ether solvent and the ester solvent are preferred, and an ether solvent and an ester solvent each having a glycol structure are more preferred in light of superior film formability.

Exemplary ether solvent and exemplary ester solvent each having a glycol structure include propylene glycol monomethyl ether, propylene glycol monoethyl ether, propylene glycol monopropyl ether, propylene glycol monomethyl ether acetate, propylene glycol monoethyl ether acetate, propylene glycol monopropyl ether acetate, and the like. Of these, propylene glycol monomethyl ether acetate is particularly preferred.

The lower limit of the percentage content of the ether solvent and the ester solvent, each having a glycol structure, in the solvent (B) is preferably 20% by mass, more preferably 60% by mass, still more preferably 90% by mass, and particularly preferably 100% by mass.

(C) Acid Generating Agent

The acid generating agent (C) generates an acid by an action of heat and/or light to promote the crosslinking of molecules of the compound (A). When the composition for resist underlayer film formation contains the acid generating agent (C), the crosslinking reaction of molecules of the compound (A) is promoted and consequently the hardness of the formed film is enabled to be further increased. The acid generating agent (C) may be used either alone of one type, or in combination of two or more types thereof.

The acid generating agent (C) is exemplified by an onium salt compound, an N-sulfonyloxyimide compound, and the like.

The onium salt compound is exemplified by a sulfonium salt, a tetrahydrothiophenium salt, an iodonium salt, an ammonium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, and the like.

Examples of the ammonium salt include triethylammonium trifluoromethanesulfonate, triethylammonium nonafluoro-n-butanesulfonate, trimethylammonium nonafluoro-n-butanesulfonate, tetraethylammonium nonafluoro-n-butanesulfonate, triethylammonium perfluoro-n-octanesulfonate, triethylammonium 2-bicyclo[2.2.1]hept-2-yl-1,1,2,2-tetrafluoroethanesulfonate, and the like.

N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, and the like.

Of these, the acid generating agent (C) is preferably the onium salt compound, more preferably the iodonium salt or the ammonium salt, and still more preferably bis(4-t-butylphenyl)iodonium nonafluoro-n-butanesulfonate or triethylammonium nonafluoro-n-butanesulfonate.

In the case in which the composition for resist underlayer film formation contains the acid generating agent (C), the lower limit of the content of the acid generating agent (C) with respect to 100 parts by mass of the compound (A) is preferably 0.1 parts by mass, more preferably 1 part by mass, and still more preferably 3 parts by mass. The upper limit of the content is preferably 20 parts by mass, more preferably 15 parts by mass, and still more preferably 12 parts by mass. When the content of the acid generating agent (C) falls within the above range, the crosslinking reaction of molecules of the compound (A) may be facilitated more effectively.

(D) Crosslinking Agent

The crosslinking agent (D) forms crosslinking bonds between components such as the compound (A) in the composition for resist underlayer film formation, or forms cross-linked structures by molecules of itself, through an action of heat and/or an acid. When the composition for resist underlayer film formation contains the crosslinking agent (D), an increase in the hardness of the formed film is enabled. The crosslinking agent (D) may be used either alone of one type, or in combination of two or more types thereof.

The crosslinking agent (D) is exemplified by a polyfunctional (meth)acrylate compound, an epoxy compound, a hydroxymethyl group-substituted phenol compound, an alkoxyalkyl group-containing phenol compound, a compound having an alkoxyalkylated amino group, a random copolymer of an acenaphthylene with hydroxymethylacenaphthylene which is represented by the following formula (7-P), compounds represented by the following formulae (11-1) to (11-12), and the like.

Examples of the polyfunctional (meth)acrylate compound include trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl)isocyanurate tri(meth)acrylate, ethylene glycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethylene glycol di(meth)acrylate, triethylene glycol di(meth)acrylate, dipropylene glycol di(meth)acrylate, bis(2-hydroxyethyl)isocyanurate di(meth)acrylate, and the like.

Examples of the epoxy compound include novolak epoxy resins, bisphenol epoxy resins, alicyclic epoxy resins, aliphatic epoxy resins, and the like.

Examples of the hydroxymethyl group-substituted phenol compound include 2-hydroxymethyl-4,6-dimethylphenol, 1,3,5-trihydroxymethylbenzene, 3,5-dihydroxymethyl-4-methoxytoluene (i.e., 2,6-bis(hydroxymethyl)-p-cresol), and the like.

Examples of the alkoxyalkyl group-containing phenol compound include methoxymethyl group-containing phenol compounds, ethoxymethyl group-containing phenol compounds, and the like.

Examples of the compound having an alkoxyalkylated amino group include nitrogen-containing compounds having a plurality of active methylol groups in a molecule thereof, wherein the hydrogen atom of the hydroxyl group of at least one of the methylol groups is substituted with an alkyl group such as a methyl group or a butyl group, and the like; examples thereof include (poly)methylolated melamines, (poly)methylolated glycolurils, (poly)methylolated benzoguanamines, (poly)methylolated ureas, and the like. It is to be noted that a mixture constituted with a plurality of substituted compounds described above may be used as the compounds having an alkoxyalkylated amino group, and the compound having an alkoxyalkylated amino group may contain an oligomer component formed through partial self-condensation thereof.

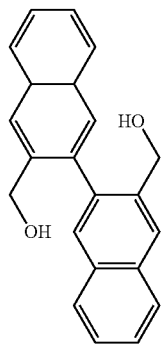
(11-P)

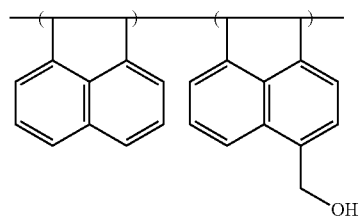
(11-1)

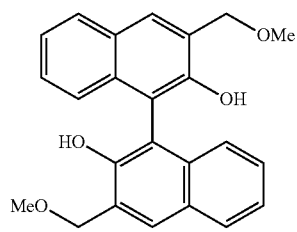
(11-2)

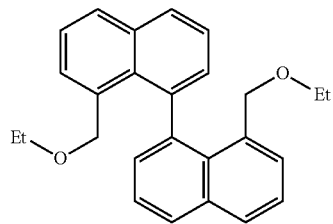
(11-3)

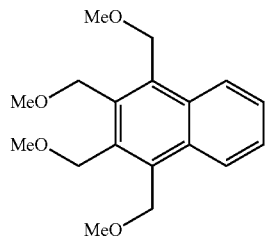
(11-4)

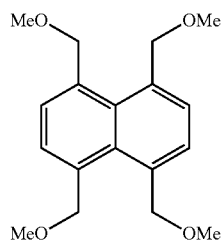
(11-5)

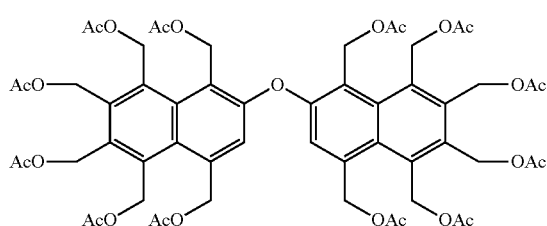
(11-6)

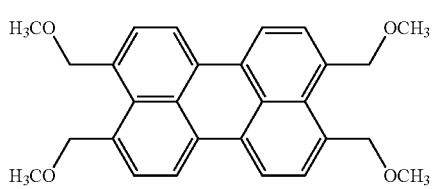
(11-7)

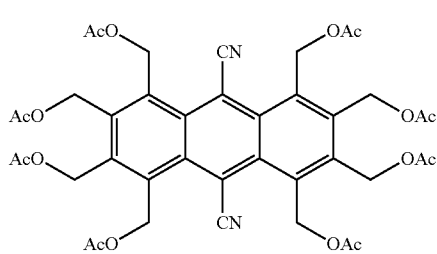
(11-8)

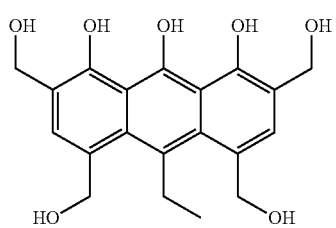
(11-9)

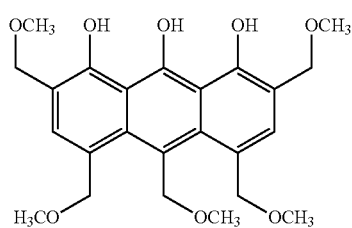
(11-10)

-continued

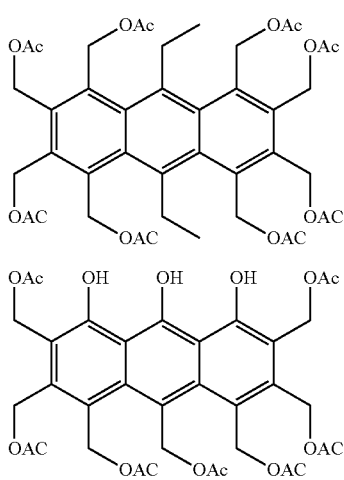

(11-11)

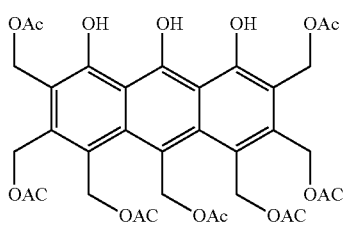

(11-12)

In the above formulae (11-6), (11-8), (11-11) and (11-12), Ac represents an acetyl group.

It is to be noted that the compounds represented by the above formulae (11-1) to (11-12) each may be synthesized with reference to the following documents.

The compound represented by the formula (11-1):
Guo, Qun-Sheng; Lu, Yong-Na; Liu, Bing; Xiao, Jian; and Li, Jin-Shan, Journal of Organometallic Chemistry, 2006, vol. 691, #6, p. 1282-1287.

The compound represented by the formula (11-2):
Badar, Y. et al., Journal of the Chemical Society, 1965, p. 1412-1418.

The compound represented by the formula (11-3):
Hsieh, Jen-Chieh; Cheng, Chien-Hong, Chemical Communications (Cambridge, United Kingdom), 2008, #26, p. 2992-2994.

The compound represented by the formula (11-4):
Japanese Unexamined Patent Application, Publication No. H5-238990.

The compound represented by the formula (11-5):
Bacon, R. G. R.; Bankhead, R., Journal of the Chemical Society, 1963, p. 839-845.

The compounds represented by the formulae (11-6), (11-8), (11-11) and (11-12):
Macromolecules, 2010, vol. 43, p. 2832-2839.

The compounds represented by the formulae (11-7), (11-9) and (11-10):
Polymer Journal, 2008, vol. 40, No. 7, p. 645-650; and Journal of Polymer Science: Part A, Polymer Chemistry, vol. 46, p. 4949-4958.

Among these crosslinking agents (D), the methoxymethyl group-containing phenol compound, the compound having an alkoxyalkylated amino group, and the random copolymer of acenaphthylene with hydroxymethylacenaphthylene are preferred, the compound having an alkoxyalkylated amino group is more preferred, and 1,3,4,6-tetra(methoxymethyl) glycoluril is still more preferred.

In the case in which the composition for resist underlayer film formation contains the crosslinking agent (D), the lower limit of the content of the crosslinking agent (D) with respect to 100 parts by mass of the compound (A) is preferably 0.1 parts by mass, more preferably 0.5 parts by mass, still more preferably 1 part by mass, and particularly preferably 3 parts by mass. The upper limit of the content is preferably 100 parts by mass, more preferably 50 parts by mass, still more preferably 30 parts by mass, and particularly preferably 20 parts by mass. When the content of the crosslinking agent (D) falls within the above range, the crosslinking reaction of molecules of the compound (A) may be allowed to occur more effectively.

Other Optional Component

Other optional component is exemplified by a surfactant, and the like.

Surfactant

When the composition for resist underlayer film formation contains the surfactant, coating characteristics thereof can be improved, and consequently uniformity of the surface of the formed film may be improved and occurrence of the unevenness of coating can be inhibited. The surfactant may be used either alone of one type, or in combination of two or more types thereof.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, and the like. Furthermore, examples of commercially available surfactant include KP341 (available from Shin-Etsu Chemical Co., Ltd.); Polyflow No. 75 and Polyflow No. 95 (each available from Kyoeisha Chemical Co., Ltd.); EFTOP EF101, EFTOP EF204, EFTOP EF303 and EFTOP EF352 (each available from Tochem Products Co. Ltd.); Megaface F171, Megaface F172 and Megaface F173 (each available from DIC Corporation); Fluorad FC430, Fluorad FC431, Fluorad FC135 and Fluorad FC93 (each available from Sumitomo 3M Limited); ASAHI GUARD AG710, Surflon S382, Surflon SC101, Surflon SC102, Surflon SC103, Surflon SC104, Surflon SC105 and Surflon SC106 (each available from Asahi Glass Co., Ltd.); and the like.

In the case in which the composition for resist underlayer film formation contains the surfactant, the lower limit of the content of the surfactant with respect to 100 parts by mass of the compound (A) is preferably 0.01 parts by mass, more preferably 0.05 parts by mass, and still more preferably 0.1 parts by mass. The upper limit of the content is preferably 10 parts by mass, more preferably 5 parts by mass, and still more preferably 1 part by mass. When the content of the surfactant falls within the above range, the coating characteristics of the composition for resist underlayer film formation is enabled to be more improved.

Preparation Procedure of Composition for Resist Underlayer Film Formation

The composition for resist underlayer film formation may be prepared, for example, by mixing the compound (A) and the solvent (B), as well as the acid generating agent (C), the crosslinking agent (D) and the other optional component as needed, at a certain ratio, preferably followed by filtering a mixture thus obtained through a membrane filter, etc. having a pore size of about 0.1 μm. The lower limit of the solid content concentration of the composition for resist underlayer film formation is preferably 0.1% by mass, more preferably 1% by mass, still more preferably 3% by mass, and particularly preferably 5% by mass. The upper limit of the solid content concentration of the composition for resist underlayer film formation is preferably 50% by mass, more preferably 30% by mass, still more preferably 20% by mass, and particularly preferably 15% by mass.

The composition for resist underlayer film formation enables a film superior in etching resistance, flatness and heat resistance to be formed with superior coating characteristics, and can therefore be suitably used for formation of a resist underlayer film in production of a semiconductor device and the like. In addition, the composition for film formation can also be used for formation of a protective film, an insulating film, a colored cured film in a display device and the like.

Resist Underlayer Film

The resist underlayer film according to the another embodiment of the present invention is formed from the composition for resist underlayer film formation according to the embodiment of the present invention. Since the resist underlayer film is formed from the composition for resist underlayer film formation having the characteristics described above, the resist underlayer film is superior in etching resistance, flatness and heat resistance.

Method for Resist Underlayer Film Formation

The method for resist underlayer film formation of the still another embodiment of the invention includes: applying the composition for resist underlayer film formation directly or indirectly on an upper face side of a substrate (hereinafter, may be also referred to as "applying step"); and heating a coating film obtained by the applying step (hereinafter, may be also referred to as "heating step"). The method for resist underlayer film formation is capable of forming a resist underlayer film that is superior in etching resistance, flatness and heat resistance since the composition for resist underlayer film formation having the characteristics described above is used.

Applying Step

In this step, the composition for resist underlayer film formation of the one embodiment of the invention is applied directly or indirectly on an upper face side of the substrate. Examples of the substrate include a silicon wafer, a wafer coated with aluminum, and the like. The applying procedure of the composition for resist underlayer film formation is not particularly limited, and for example, an appropriate procedure such as spin coating, cast coating and roll coating may be employed to form a coating film.

Heating Step

In this step, the coating film obtained by the applying step is heated. The resist underlayer film is thus formed.

Heating of the coating film is typically carried out in an ambient air. The lower limit of a heating temperature is preferably 150° C., more preferably 200° C., and still more preferably 250° C. The upper limit of the heating temperature is preferably 500° C., more preferably 450° C., and still more preferably 400° C. When the heating temperature is less than 150° C., oxidative crosslinking may not sufficiently proceed, and characteristics necessary for use in the resist underlayer film may not be exhibited. The lower limit of the heating time period is preferably 15 sec, more preferably 30 sec, and still more preferably 45 sec. The upper limit of the heating time period is preferably 1,200 sec, more preferably 600 sec, and still more preferably 300 sec.

The coating film may be preheated at a temperature of no less than 60° C. and no greater than 250° C. before being heated at a temperature of no less than 150° C. and no greater than 500° C. The lower limit of the heating time period in the preheating is preferably 10 sec, and more preferably 30 sec. The upper limit of the heating time period is preferably 300 sec, and more preferably 180 sec. When the preheating is carried out to preliminarily evaporate a solvent and make the film dense, a dehydrogenation reaction during the subsequent heating may efficiently proceed.

It is to be noted that in the method for resist underlayer film formation, the resist underlayer film is formed through the heating of the coating film; however, in a case in which the composition for resist underlayer film formation contains the acid generating agent (C) and the acid generating agent (C) is a radiation-sensitive acid generating agent, the resist underlayer film may be formed also by hardening the film through a combination of an exposure and heating. The radioactive ray used for the exposure may be appropriately selected from: electromagnetic waves such as visible rays, ultraviolet rays, far ultraviolet rays, X-rays and γ radiations; particle rays such as electron beams, molecular beams and ion beams, and the like in accordance with the type of the acid generating agent (C).

The lower limit of the average thickness of the resist underlayer film formed is preferably 50 nm, more preferably 100 nm, and still more preferably 200 nm. The upper limit of the average thickness of the resist underlayer film formed is preferably 3,000 nm, more preferably 2,000 nm, and still more preferably 500 nm.

Production Method of Patterned Substrate

The production method of a patterned substrate according to the yet another embodiment of the present invention includes: forming a resist pattern directly or indirectly on an upper face side of the resist underlayer film obtained by the method for resist underlayer film formation according to the still another embodiment of the invention (hereinafter, may be also referred to as "resist pattern-forming step"); and carrying out etching using the resist pattern as a mask (hereinafter, may be also referred to as "etching step").

According to the production method of a patterned substrate, use of the resist underlayer film that is superior in etching resistance, flatness and heat resistance obtained by the aforementioned resist underlayer film-forming method enables a patterned substrate having a superior pattern configuration to be obtained.

Before the resist pattern-forming, the production method of a patterned substrate may include as needed, forming an intermediate layer (intermediate film) directly or indirectly on the resist underlayer film. Hereinafter, each step is explained.

Intermediate Layer-Forming Step

In this step, an intermediate layer is formed directly or indirectly on the upper face side of the resist underlayer film. The intermediate layer as referred to means a layer having a function that is exhibited or not exhibited by the resist underlayer film and/or the resist film in resist pattern formation in order to further enhance the function exhibited by the resist underlayer film and/or the resist film, or to impart to the resist underlayer film and/or the resist film a function not exhibited thereby. For example, when an antireflective film is provided as the intermediate layer, an antireflecting function of the resist underlayer film may be further enhanced.

The intermediate layer may be formed from an organic compound and/or an inorganic oxide. Examples of the organic compound include commercially available products such as: "DUV-42", "DUV-44", "ARC-28" and "ARC-29" (each available from Brewer Science); "AR-3" and "AR-19" (each available from Lohm and Haas Company); and the like. Examples of the inorganic oxide include commercially available products such as "NFC SOG01", "NFC SOG04" and "NFC SOG080" (each available from JSR Corporation), and the like. As the inorganic oxide, polysiloxanes, titanium oxides, alumina oxides, tungsten oxides, and the like that are provided through a CVD process may also be used.

The forming procedure of the intermediate layer is not particularly limited, and for example, a coating procedure, a CVD technique, or the like may be employed. Of these, the coating procedure is preferred. In a case in which the coating procedure is employed, the intermediate layer may be successively provided after the resist underlayer film is formed.

Moreover, the average thickness of the intermediate layer is appropriately selected in accordance with the function required for the intermediate layer, and the lower limit of the average thickness of the intermediate layer is preferably 10 nm, and more preferably 20 nm. The upper limit of the average thickness of the intermediate layer is preferably 3,000 nm, and more preferably 300 nm.

Resist Pattern-Forming Step

In this step, a resist pattern is formed directly or indirectly on the upper face side of the resist underlayer film. In the case in which the intermediate layer-forming step is carried out, a resist pattern is formed directly or indirectly on the upper face side of the intermediate layer. This step may be carried out by, for example, using a resist composition.

When the resist composition is used, specifically, the resist film is formed by applying the resist composition such that a resultant resist film has a predetermined thickness and thereafter subjecting the resist composition to prebaking to evaporate the solvent in the coating film.

Examples of the resist composition include a chemically amplified positive or negative resist composition that contains a radiation-sensitive acid generating agent; a positive resist composition containing an alkali-soluble resin and a quinone diazide-based photosensitizing agent; a negative resist containing an alkali-soluble resin and a crosslinking agent; and the like.

The lower limit of the solid content concentration of the resist composition is preferably 0.3% by mass, and more preferably 1% by mass. The upper limit of the solid content concentration of the resist composition is preferably 50% by mass, and more preferably 30% by mass. Moreover, the resist composition is generally used for forming a resist film, for example, after being filtered through a filter with a pore size of 0.2 µm. It is to be noted that a commercially available resist composition may be used as is in this step.

The applying procedure of the resist composition is not particularly limited, and examples thereof include a spin-coating method, and the like. The temperature of the prebaking may be appropriately adjusted in accordance with the type of the resist composition employed and the like; however, the lower limit of the temperature is preferably 30° C., and more preferably 50° C. The upper limit of the aforementioned temperature is preferably 200° C., and more preferably 150° C. The lower limit of a time period for the prebaking is preferably 10 sec, and more preferably 30 sec. The upper limit of the time period for the prebaking is preferably 600 sec, and more preferably 300 sec.

Next, the resist film formed is exposed by selective irradiation with a radioactive ray. The radioactive ray used in the exposure may be appropriately selected from: electromagnetic waves such as visible rays, ultraviolet rays, far ultraviolet rays, X-rays and γ radiations; particle rays such as electron beams, molecular beams and ion beams in accordance with the type of the radiation-sensitive acid generating agent used in the resist composition. Among these, far ultraviolet rays are preferred, and a KrF excimer laser beam (248 nm), and an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm) and extreme ultraviolet rays (EUV; wavelength: 13.5 nm, etc.) are more preferred, and a KrF excimer laser beam, an ArF excimer laser beam and EUV are still more preferred.

Post-baking may be carried out after the exposure for the purpose of improving a resolution, a pattern profile, developability, and the like. The temperature of the post-baking may be appropriately adjusted in accordance with the type of the resist composition employed and the like; however, the lower limit of the temperature is preferably 50° C., and more preferably 70° C. The upper limit of the aforementioned temperature is preferably 200° C., and more preferably 150° C. The lower limit of a time period for the post-baking is preferably 10 sec, and more preferably 30 sec. The upper limit of the time period for the post-baking is preferably 600 sec, and more preferably 300 sec.

Next, the resist film exposed is developed with a developer solution to form a resist pattern. The development may be either a development with an alkali or a development with an organic solvent. In the case of the development with an alkali, examples of the developer solution include an alkaline aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water soluble organic solvent, e.g., an alcohol such as methanol and ethanol, a surfactant, and the like may be added to the alkaline aqueous solution. Alternatively, in the case of the development with an organic solvent, examples of the developer solution include a variety of organic solvents exemplified as the solvent (B) in relation to the composition for resist underlayer film formation described above, and the like.

A predetermined resist pattern is formed by the development with the developer solution, followed by washing and drying.

In carrying out the resist pattern-forming step, without using the resist composition described above, other process may be employed, for example, a nanoimprint method may be adopted, or a directed self-assembling composition may be used.

Etching Step

In this step, etching is carried out with the aforementioned resist pattern as a mask to form a pattern on a substrate. The etching may be carried out once or multiple times. In other words, the etching may be carried out sequentially with patterns obtained by the etching as masks. However, in light of obtaining a pattern with a favorable shape, the etching is preferably carried out multiple times. When the etching is carried out multiple times, in a case in which the intermediate layer is not provided, the resist underlayer film and the substrate are subjected to etching sequentially in this order, whereas in a case in which the intermediate layer is provided, the intermediate layer, the resist underlayer film and the substrate are subjected to etching sequentially in this order. The etching step may be exemplified by dry etching, wet etching, and the like. Of these, in light of achieving a pattern with a more favorable shape, dry etching is preferred. For example, gas plasma such as oxygen plasma and the like may be used as the dry etching. After the dry etching, the substrate having a predetermined pattern can be obtained.

Compound

The compound according to the yet still another embodiment of the invention has the group (I). Owing to having the characteristics described above, the compound can be suitably used as a component of the composition for resist underlayer film formation. The compound has been described as the compound (A) in the section of Composition for Resist Underlayer Film Formation above.

EXAMPLES

Hereinafter, the embodiment of the present invention will be explained in more detail by way of Examples, but the present invention is not in any way limited to these Examples. Measuring methods for various types of physical properties are shown below.

Mw and Mn

In the case in which the compound (A) is a resin, the Mw and the Mn of the compound (A) were each determined by gel permeation chromatography using GPC columns ("G2000 HXL"×2, and "G3000 HXL"×1) available from Tosoh Corporation, a differential refractometer as a detector and mono-dispersed polystyrene as a standard under analytical conditions involving a flow rate of 1.0 mL/min, an elution solvent of tetrahydrofuran and a column temperature of 40° C.

Average Thickness of Film

The average thickness of the film was determined using a spectroscopic ellipsometer ("M2000D" available from J. A. WOOLLAM Co.).

Synthesis of Compound (A)

Compounds represented by the following formulae (A-1) to (A-10) were synthesized by the following procedure. It is to be noted that the content of oxygen atoms in the compound (A) shown in Table 1 is a value determined from the structure of the compound.

(A-1)

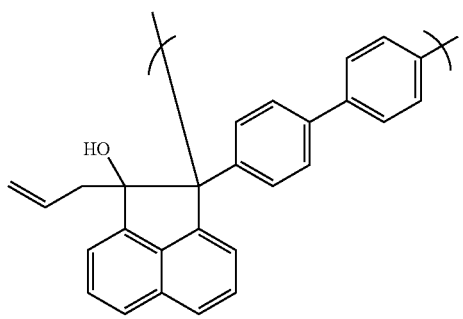

(A-2)

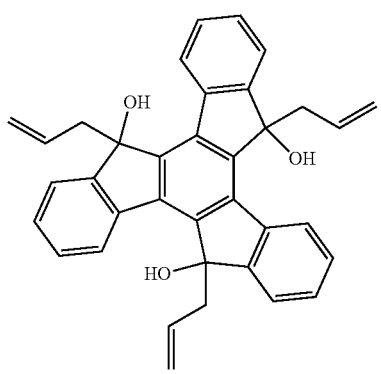

(A-3)

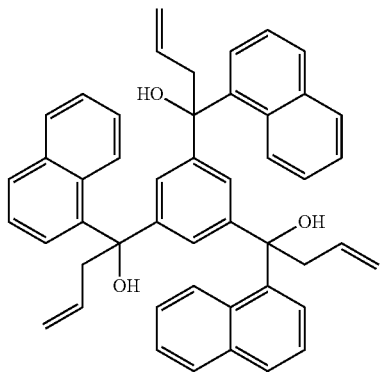

(A-4)

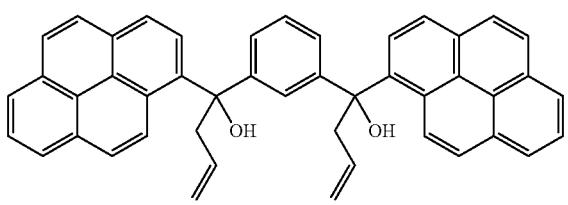

(A-5)

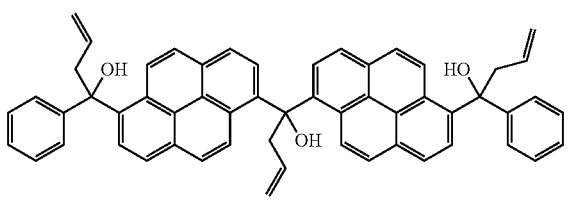

(A-6)

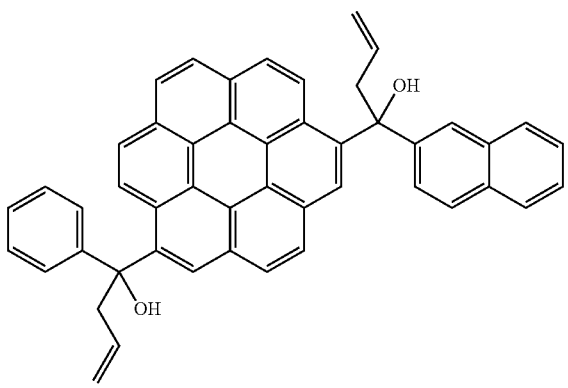

(A-7)

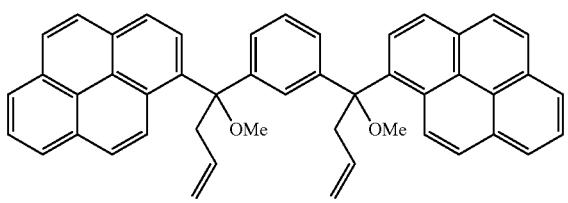

(A-8)

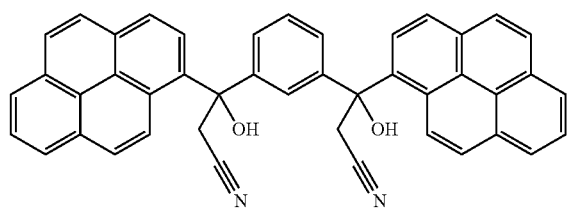

(A-9)

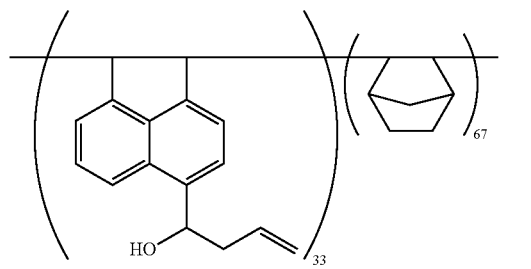

(A-10)

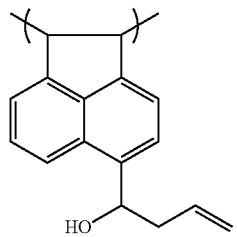

The compounds (A-1), (A-9) and (A-10) were resins having the structural units represented by the above formulae, respectively.

Example 1-1

Into a 500-mL three-neck flask equipped with a thermometer, a condenser and a magnetic stirrer were charged 23.63 g of acenaphthene quinone, 20.0 g of biphenyl and 130 g of dichloromethane in a nitrogen atmosphere, and dissolution was allowed. Subsequently, 17.75 g of trifluoroacetic acid and 23.36 g of trifluoromethanesulfonic acid were added and the mixture was stirred at 20° C. for 12 hrs to conduct polymerization. Thereafter, the polymerization reaction mixture was charged into a large quantity of methanol, and filtration of a resin precipitated, followed by drying under reduced pressure at 60° C. overnight gave a resin represented by the following formula (B-1). Next, into a 500-mL three-neck flask equipped with a thermometer, a condenser and a magnetic stirrer were charged 40 g of the resin (B-1) and 120 g of tetrahydrofuran in a nitrogen atmosphere, and dissolution was allowed at room temperature. After the mixture was cooled to 0° C., 155 g of a tetrahydrofuran solution of allylmagnesium chloride (1 M) was added thereto dropwise over 0.5 hrs. After completion of the dropwise addition, the mixture was heated to 60° C. and subjected to a reaction for 3 hrs. After completion of the reaction, a large quantity of water was added to the reaction mixture, and then 120 g of methyl isobutyl ketone was added thereto to perform extraction. Thus resulting organic layer was washed with water twice and thereafter charged into 600 g of hexane to permit reprecipitation. The precipitate thus obtained was filtered off and then dried under reduced pressure at 60° C. overnight to give the compound (A-1) (yield 78%). The compound (A-1) had the Mw of 1,500.

(B-1)

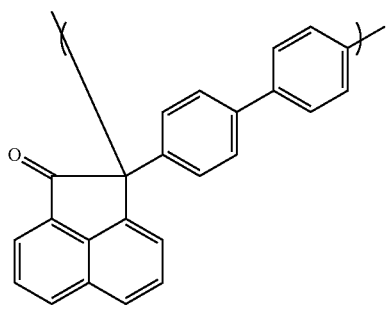

Example 1-2

Into a 500-mL three-neck flask equipped with a thermometer, a condenser and a magnetic stirrer were charged 15 g of a compound represented by the following formula (B-2) and 120 g of tetrahydrofuran in a nitrogen atmosphere, and dissolution was allowed at room temperature. After the mixture was cooled to 0° C., 155 g of a tetrahydrofuran solution of allylmagnesium chloride (1 M) was added thereto dropwise over 0.5 hrs. After completion of the dropwise addition, the mixture was heated to 60° C. and subjected to a reaction for 3 hrs. After completion of the reaction, a large quantity of water was added to the reaction mixture, and then 120 g of methyl isobutyl ketone was added thereto to perform extraction. Thus resulting organic layer was washed with water twice and thereafter charged into 600 g of hexane to permit reprecipitation. The precipitate thus obtained was filtered off and then dried under reduced pressure at 60° C. overnight to give the compound (A-2) (yield 80%).

Example 1-3

The compound (A-3) was synthesized in a similar manner to Example 1-2 except that a compound represented by the following formula (B-3) was used in place of the compound (B-2).

Example 1-4

Into a 500-mL three-neck flask equipped with a thermometer, a condenser and a magnetic stirrer were charged 40 g of a compound represented by the following formula (B-4) and 120 g of tetrahydrofuran in a nitrogen atmosphere, and dissolution was allowed at room temperature. After the mixture was cooled to 0° C., 155 g of a tetrahydrofuran solution of allylmagnesium chloride (1 M) was added thereto dropwise over 0.5 hrs. After completion of the dropwise addition, the mixture was heated to 60° C. and subjected to a reaction for 3 hrs. After completion of the reaction, a large quantity of water was added to the reaction mixture, and then 120 g of methyl isobutyl ketone was added thereto to perform extraction. Thus resulting organic layer was washed with water twice and thereafter charged into 600 g of hexane to permit reprecipitation. The precipitate thus obtained was filtered off and then dried under reduced pressure at 60° C. overnight to give the compound (A-4).

Example 1-5

The compound (A-5) was synthesized in a similar manner to Example 1-2 except that a compound represented by the following formula (B-5) was used in place of the compound (B-2).

Example 1-6

The compound (A-6) was synthesized in a similar manner to Example 1-4 except that a compound represented by the following formula (B-6) was used in place of the compound (B-4).

Example 1-7

Into a 500-mL three-neck flask equipped with a thermometer, a condenser and a magnetic stirrer were charged 40 g of the compound (A-4) and 200 g of tetrahydrofuran in a nitrogen atmosphere, and dissolution was allowed at room temperature. After the mixture was cooled to 0° C., 15 g of an oil dispersion of sodium hydride (60% by mass) was added thereto and a reaction was allowed for 1 hour. After adding 46 g of methyl iodide, the mixture was subjected to a reaction at 0° C. for 1 hour. After completion of the reaction, a large quantity of water was added to the reaction mixture, and then 120 g of methyl isobutyl ketone was added thereto to perform extraction. Thus resulting organic layer was washed with water twice and thereafter charged into 600 g of hexane to permit reprecipitation. The precipitate thus obtained was filtered off and then dried under reduced pressure at 60° C. overnight to give the compound (A-7) (yield 84%).

Example 1-8

Into a 500-mL three-neck flask equipped with a thermometer, a condenser and a magnetic stirrer was charged 190 g of a cyclohexane solution of n-butyllithium (2.3 M) in a nitrogen atmosphere, followed by cooling to −78° C. After 18 g of tetramethylethylene diamine was added to the solution, 36 g of propargyl bromide was added dropwise thereto and the mixture was stirred for 20 min. To this solution, 40 g of a tetrahydrofuran solution of 40 g of a compound represented by the following formula (B-4) was added dropwise and the temperature of the mixture was raised to room temperature over 2 hrs. After completion of the reaction, a large quantity of water was added to the reaction mixture, and then 120 g of methyl isobutyl ketone was added thereto to perform extraction. Thus resulting organic layer was washed with water twice and thereafter charged into 600 g of hexane to permit reprecipitation. The precipitate thus obtained was filtered off and then dried under reduced pressure at 60° C. overnight to give the compound (A-8) (yield 83%).

Example 1-9

Into a reactor, i.e., a 5,000-mL three-neck flask equipped with a thermometer, a condenser and a magnetic stirrer were charged 0.2 mol 1-formylacenaphthylene and 0.6 mol norbornene in a nitrogen atmosphere, which were dissolved in 1,2-dichloroethane in amount of three times by mass the total mass of 1-formylacenaphthylene and norbornene, and then the mixture was stirred for 30 min. Into the mixture, 0.01 mol AIBN was gradually charged to allow a reaction at 70° C. for about 12 hrs. Thus, a resin represented by the following formula (B-7) was obtained as an intermediate. Thereafter, 0.07 mol allyl magnesiumbromide was gradually added to the mixture. After the reaction was allowed while the normal temperature was maintained for 3 hrs, 300 mL of distilled water was added thereto to terminate the reaction. The organic layer was washed with sufficient water, and thereafter only the organic layer was separated. A small amount of moisture was removed over anhydrous magnesium sulfate. The solid was filtered off and a solvent was removed from thus obtained solution under a reduced pressure to give the compound (A-9). The compound (A-9) had the Mw of 4,300.

Example 1-10

Into a 500-mL three-neck flask equipped with a thermometer, a condenser and a magnetic stirrer were charged 36 g of 1-formylacenaphthylene (200 mmol) and 1,2-dichloroethane in an amount of three times by mass the mass of 1-formylacenaphthylene in a nitrogen atmosphere, and dissolution was allowed, followed by stirring of the mixture for 30 min. Into the mixture, 20 mmol AIBN was gradually charged to allow a reaction at 70° C. for about 12 hrs. After completion of the reaction, a large quantity of water was added to the reaction mixture to perform extraction. Thus resulting organic layer was washed with water twice and thereafter charged into 600 g of hexane to permit reprecipitation. The precipitate thus obtained was filtered off and then dried under reduced pressure at 60° C. overnight to give a resin represented by the following formula (B-8).

Next, into a 500-mL three-neck flask equipped with a thermometer, a condenser and a magnetic stirrer were charged 15 g of the resin (B-8) and 120 g of tetrahydrofuran in a nitrogen atmosphere, and dissolution was allowed at room temperature. After the mixture was cooled to 0° C., 155 g of a tetrahydrofuran solution of allylmagnesium chloride (1 M) was added thereto dropwise over 0.5 hrs. After completion of the dropwise addition, the mixture was heated to 60° C. and subjected to a reaction for 3 hrs. After completion of the reaction, a large quantity of water was added to the reaction mixture, and then 120 g of methyl isobutyl ketone was added thereto to perform extraction. Thus resulting organic layer was washed with water twice and thereafter charged into 600 g of hexane to permit reprecipitation. The precipitate thus obtained was filtered off and then dried under reduced pressure at 60° C. overnight to give the compound (A-10). The compound (A-10) had the Mw of 1,500.

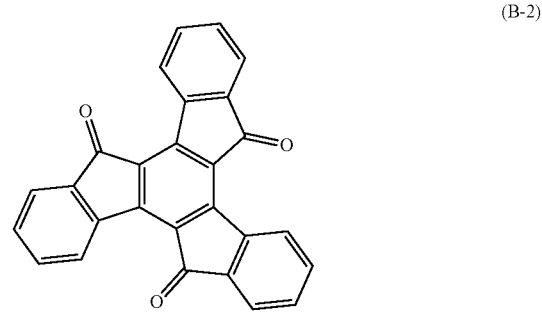

(B-2)

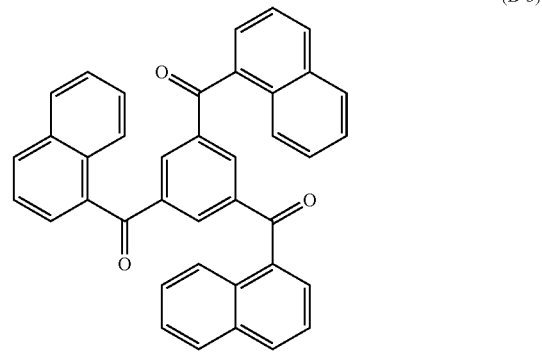

(B-3)

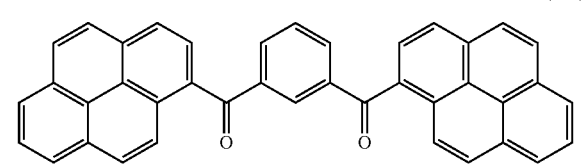

(B-4)

-continued (B-5)
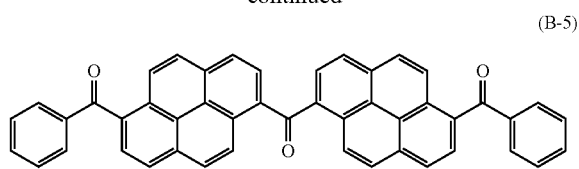

(a-1)
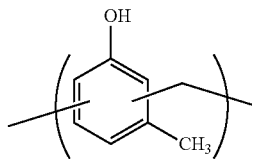

Preparation of Composition for Resist Underlayer Film Formation

The solvent (B), the acid generating agent (C) and the crosslinking agent (D) used in preparation of the composition for resist underlayer film formation are shown below.

(B) Solvent

B-1: propylene glycol monomethyl ether acetate (C) Acid Generating Agent

C-1: bis(4-t-butylphenyl)iodonium nonafluoro-n-butane-sulfonate (compound represented by the following formula (C-1))

(B-6)
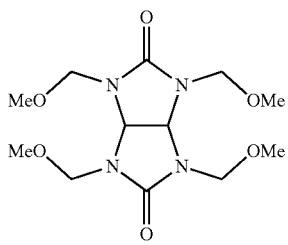

(C-1)
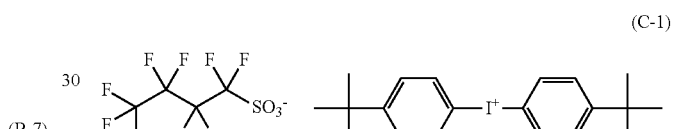

(B-7)
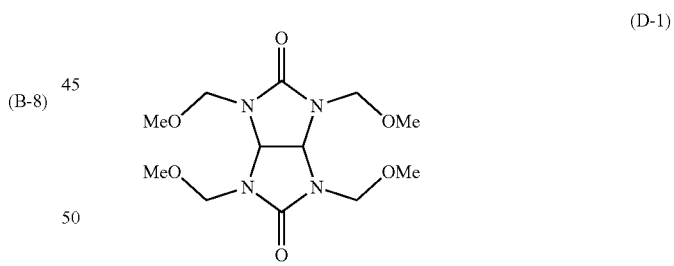

(D) Crosslinking Agent

D-1: 1,3,4,6-tetrakis(methoxymethyl)glycoluril (compound represented by the following formula (D-1))

(D-1)
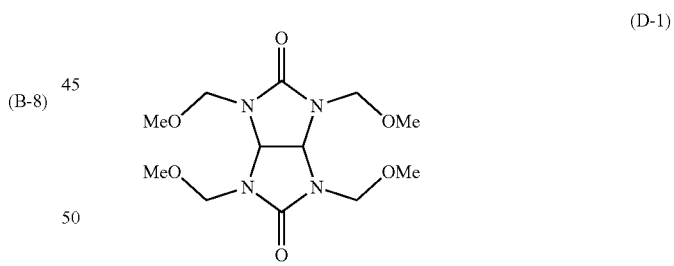

(B-8)
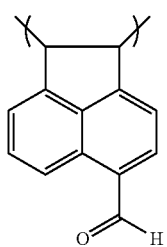

Example 2-1

In 90 parts by mass of (B-1) as the solvent (B), 10 parts by mass of (A-1) as the compound (A) and 0.5 parts by mass of (C-1) as the acid generating agent (C) were dissolved. The solution thus obtained was filtered through a membrane filter having a pore size of 0.1 μm, whereby a composition for resist underlayer film formation (J-1) was prepared.

Synthesis Example 1-1

Into a 500-mL three-neck flask equipped with a thermometer, a condenser and a magnetic stirrer were charged 250 g of m-cresol, 125 g of 37% by mass formalin and 2 g of anhydrous oxalic acid in a nitrogen atmosphere, and the reaction was allowed at 100° C. for 3 hrs and at 180° C. for 1 hour. Unreacted monomer was thereafter eliminated under a reduced pressure to give a resin represented by the following formula (a-1). The resulting resin (a-1) had the Mw of 11,000, and the Mw/Mn of 8.4.

Examples 2-2 to 2-12 and Comparative Example 2-1

Compositions for resist underlayer film formation (J-2) to (J-13) were prepared by a similar operation to that of Example 2-1 except that each component of the type and the content shown in Table 1 below was used. In Table 1, "-" indicates that the corresponding component was not used.

TABLE 1

| | Composition for resist underlayer film formation | (A) Compound | | | (B) Solvent | | (C) Acid generating agent | | (D) Crosslinking agent | |
|---|---|---|---|---|---|---|---|---|---|---|
| | | type | content (parts by mass) | oxygen atom content (% by mass) | type | content (parts by mass) | type | content (parts by mass) | type | content (parts by mass) |
| Example 2-1 | J-1 | A-1 | 10 | 4.1 | B-1 | 90 | C-1 | 0.5 | — | — |
| Example 2-2 | J-2 | A-2 | 10 | 9.4 | B-1 | 90 | C-1 | 0.5 | — | — |
| Example 2-3 | J-3 | A-3 | 10 | 7.2 | B-1 | 90 | C-1 | 0.5 | — | — |
| Example 2-4 | J-4 | A-4 | 10 | 5.1 | B-1 | 90 | C-1 | 0.5 | — | — |
| Example 2-5 | J-5 | A-5 | 10 | 6.3 | B-1 | 90 | C-1 | 0.5 | — | — |
| Example 2-6 | J-6 | A-6 | 10 | 5.0 | B-1 | 90 | C-1 | 0.5 | — | — |
| Example 2-7 | J-7 | A-7 | 10 | 5.0 | B-1 | 90 | C-1 | 0.5 | — | — |
| Example 2-8 | J-8 | A-8 | 10 | 5.2 | B-1 | 90 | C-1 | 0.5 | — | — |
| Example 2-9 | J-9 | A-9 | 10 | 3.9 | B-1 | 90 | C-1 | 0.5 | — | — |
| Example 2-10 | J-10 | A-10 | 10 | 7.2 | B-1 | 90 | C-1 | 0.5 | — | — |
| Example 2-11 | J-11 | A-1 | 10 | 4.1 | B-1 | 90 | C-1 | 0.5 | D-1 | 1 |
| Example 2-12 | J-12 | A-1 | 10 | 4.1 | B-1 | 90 | — | — | — | — |
| Comparative Example 2-1 | J-13 | a-1 | 10 | 13.3 | B-1 | 90 | C-1 | 0.5 | D-1 | 3 |

Formation of Resist Underlayer Film

Examples 3-1 to 3-12 and Comparative Example 3-1

The compositions for resist underlayer film formation prepared as described above were each applied on a silicon wafer substrate by way of a spin-coating procedure. Thereafter, heating (baking) was carried out at the heating temperature (° C.) for the heating time period (sec) shown in Table 2 below in an ambient air atmosphere to form a resist underlayer film having a thickness of 200 nm, whereby substrates having the resist underlayer film formed thereon were obtained. In Table 2, "-" indicates that Comparative Example 3-1 serves as a standard for etching resistance evaluation.

Evaluations

For the compositions for resist underlayer film formation and the substrates provided with a resist underlayer film obtained as described above, the following evaluations were each made according to the following procedures. The results of the evaluations are shown in Table 2 below.

Coating Characteristics

With respect to the substrate provided with a resist underlayer film, the presence/absence of a streak defect (striation) from the center toward the circumferential direction was visually observed. The coating characteristics was evaluated to be: "A" (favorable) in the case of no streak defect (striation) being present; and "B" (unfavorable) in the case of the defect being present.

Etching Resistance

The resist underlayer film of the substrate provided with the resist underlayer film obtained as described above was treated in an etching apparatus ("TACTRAS" available from Tokyo Electron Limited) under conditions involving: CF$_4$/Ar=110/440 sccm, PRESS.=30 MT, HF RF (radiofrequency power for plasma production)=500 W, LF RF (radiofrequency power for bias)=3,000 W, DCS=−150 V, RDC (flow rate percentage at gas center)=50%, and 30 sec. An etching rate (nm/min) was calculated based on the average thickness of the resist underlayer film before the treatment and the average thickness of the resist underlayer film after the treatment, and the ratio of the etching rate of the resist underlayer film of each Example to Comparative Example 3-1 was calculated as a standard for etching resistance evaluation. The etching resistance was evaluated to be: "A" (extremely favorable) in the case of the ratio being no less than 0.95 and less than 0.98; "B" (favorable) in the case of the ratio being no less than 0.98 and less than 1.00; and "C" (unfavorable) in the case of the ratio being no less than 1.00.

Flatness

Each of the prepared compositions for resist underlayer film formation was applied by a spin-coating procedure using a spin coater ("CLEAN TRACK ACT-12" available from Tokyo Electron Limited), on a silicon substrate 1 provided with a trench pattern having a depth of 100 nm and a groove width of 10 μm formed thereon, as shown in the FIGURE. The rotational speed for the spin coating was the same as that in the case of forming the resist underlayer film having the average thickness of 200 nm in the "Formation of Resist Underlayer Film" described above. Subsequently, the resulting substrate was heated (baked) at 250° C. for 60 sec in an ambient air atmosphere to form a film 2 having an average thickness of 200 nm at parts having been no trench was provided, whereby the silicon substrate having a film formed thereon was obtained, the silicon substrate being covered by the film.

The cross-sectional shape of the silicon substrate having the film formed thereon was observed by using a scanning electron microscope ("S-4800" available from Hitachi High-Technologies Corporation), and the difference (ΔFT) between the height at the center portion of the trench pattern "b" of the resist underlayer film and the height at a position 5 μm away from the edge of the trench pattern, at which no trench pattern was provided "a", was defined as a marker of the flatness. The flatness was evaluated to be "A" (extremely favorable) in the case of ΔFT being less than 40 nm, "B" (favorable) in the case of ΔFT being no less than 40 nm and less than 60 nm, and "C" (unfavorable) in the case of ΔFT being no less than 60 nm. It is to be noted that the difference in heights shown in the FIGURE is exaggerated.

Heat Resistance

The composition for resist underlayer film formation prepared as described above was applied on a silicon wafer having a diameter of 8 inches by a spin-coating procedure, and baked in an ambient air atmosphere at 250° C. for 60 sec to form a resist underlayer film, whereby a substrate provided with a resist underlayer film was obtained. Next, the resist underlayer film of this substrate provided with a resist underlayer film was shaved to collect the powder, and the powder of the resist underlayer film was placed into a container for use in the measurement by a TG-DTA apparatus (NETZSCH, "TG-DTA2000SR"), and the mass before heating was measured. Subsequently, by using the TG-DTA apparatus, the film was heated to 400° C. at a rate of temperature rise of 10° C./min in a nitrogen atmosphere, and the mass of the powder at 400° C. was measured. In addition, a percent decrease of the mass (%) was determined according to the following equation, and this percent decrease of the mass was defined as a measure of the heat resistance.

$$M_L = \{(m1-m2)/m1\} \times 100$$

wherein, in the above equation, $M_L$ represents a percent decrease of the mass (%); m1 represents the mass (mg) before heating; and m2 represents the mass (mg) at 400° C.

The heat resistance is more favorable when the percent decrease of the mass of the powder to be a sample is smaller, due to less sublimation matter generated during the heating of the resist underlayer film and/or less decomposed matter of the resist underlayer film. In other words, a smaller percent decrease of the mass indicates superior heat resistance. The heat resistance was evaluated to be "A" (extremely favorable) in the case of the percent decrease of the mass being less than 5%; "B" (favorable) in the case of the percent decrease being no less than 5% and less than 10%; and "C" (unfavorable) in the case of the percent decrease being no less than 10%.

TABLE 2

|  | Composition for resist underlayer film formation | Heating temperature/ heating time in resist underlayer film formation (° C./sec) | Coating characteristics | Etching resistance | Flatness | Heat resistance |
|---|---|---|---|---|---|---|
| Example 3-1 | J-1 | 400/60 | A | A | A | A |
| Example 3-2 | J-2 | 400/60 | A | A | A | A |
| Example 3-3 | J-3 | 400/60 | A | A | A | A |
| Example 3-4 | J-4 | 400/60 | A | A | A | A |
| Example 3-5 | J-5 | 400/60 | A | A | A | A |
| Example 3-6 | J-6 | 400/60 | A | A | A | A |
| Example 3-7 | J-7 | 400/60 | A | A | A | A |
| Example 3-8 | J-8 | 400/60 | A | A | A | A |
| Example 3-9 | J-9 | 400/60 | A | B | B | B |
| Example 3-10 | J-10 | 400/60 | A | B | A | B |
| Example 3-11 | J-11 | 400/60 | A | B | A | B |
| Example 3-12 | J-12 | 400/60 | A | B | B | B |
| Comparative Example 3-1 | J-13 | 400/60 | A | — | C | C |

As is seen from the results shown in Table 2, the compositions for resist underlayer film formation of Examples enabled resist underlayer films having etching resistance, flatness and heat resistance to be formed with superior coating characteristics being exhibited.

The composition for resist underlayer film formation according to the one embodiment of the present invention enables a resist underlayer film that is superior in etching resistance, flatness and heat resistance to be formed with superior coating characteristics being exhibited. The resist underlayer film according to the another embodiment of the present invention is superior in etching resistance, flatness and heat resistance. The method for resist underlayer film formation according to the still another embodiment of the present invention is capable of forming a resist underlayer film that is superior in etching resistance, flatness and heat resistance, with superior coating characteristics being exhibited. The production method of a patterned substrate according to the yet another embodiment of the present invention enables a substrate having a favorable pattern configuration to be obtained by using the superior resist underlayer film formed. The compound according to the yet still another embodiment of the present invention can be suitably used as a component of the composition for resist underlayer film formation according to the one embodiment of the present invention. Therefore, these can be suitably used for manufacture, etc., of semiconductor devices in which further progress of microfabrication is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A composition for resist underlayer film formation comprising:
   a compound comprising a group represented by formula (1); and
   a solvent,

(1)

wherein, in the formula (1),
   $R^1$ represents an organic group having 2 to 10 carbon atoms and having a valency of (m+n), wherein the carbon atoms comprise two carbon atoms that are adjacent to each other, with a hydroxy group or an alkoxy group bonding to one of the two carbon atoms, and with a hydrogen atom bonding to another of the two carbon atoms, and wherein a hydrogen atom does not bond to the carbon atom to which the hydroxy group or the alkoxy group bonds;
   $L^1$ represents an ethynediyl group or a substituted or unsubstituted ethenediyl group;
   $R^2$ represents a hydrogen atom or a monovalent organic group having 1 to 20 carbon atoms;
   n is an integer of 1 to 3, wherein in a case where n is no less than 2, a plurality of $L^1$s are identical or different, and a plurality of $R^2$s are identical or different;
   * denotes a bonding site to a moiety other than the group represented by the formula (1) in the compound; and
   m is an integer of 1 to 3.

2. The composition according to claim 1, wherein a content of oxygen atoms in the compound is no less than 4% by mass.

3. The composition according to claim 1, wherein the compound comprises an aromatic ring.

4. The composition according to claim 1, further comprising an acid generating agent.

5. The composition according to claim 1, wherein the group represented by the formula (1) is represented by formula (1-1) or (1-2):

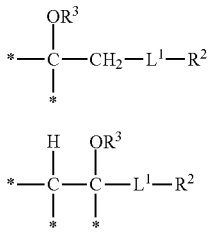

wherein, in the formulae (1-1) and (1-2),
$R^3$s each independently represent a hydrogen atom or an alkyl group having 1 to 8 carbon atoms; and
$L^1$, $R^2$ and * are as defined in the formula (1).

6. The composition according to claim 1, wherein a content of the compound in the composition is no less than 1% by mass and no greater than 50% by mass.

7. A resist underlayer film formed from the composition according to claim 1.

8. A method for resist underlayer film formation comprising:
applying the composition according to claim 1 directly or indirectly on an upper face side of a substrate to form a coating film; and
heating the coating film.

9. The method according to claim 8, wherein a content of oxygen atoms in the compound is no less than 4% by mass.

10. The method according to claim 8, wherein the compound comprises an aromatic ring.

11. The method according to claim 8, wherein the composition comprises an acid generating agent.

12. The method according to claim 8, wherein the group represented by the formula (1) is represented by formula (1-1) or (1-2):

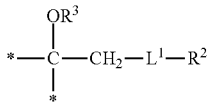

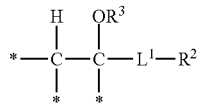

wherein, in the formulae (1-1) and (1-2),
$R^3$s each independently represent a hydrogen atom or an alkyl group having 1 to 8 carbon atoms; and
$L^1$, $R^2$ and * are as defined in the formula (1).

13. The method according to claim 8, wherein a content of the compound in the composition is no less than 1% by mass and no greater than 50% by mass.

14. A production method of a patterned substrate comprising:
forming a resist pattern directly or indirectly on an upper face side of the resist underlayer film obtained by the method according to claim 8; and
carrying out etching using the resist pattern as a mask.

15. The production method according to claim 14, wherein a content of oxygen atoms in the compound is no less than 4% by mass.

16. The production method according to claim 14, wherein the compound comprises an aromatic ring.

17. The production method according to claim 14, wherein the composition comprises an acid generating agent.

18. The production method according to claim 14, wherein the group represented by the formula (1) is represented by formula (1-1) or (1-2):

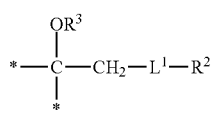

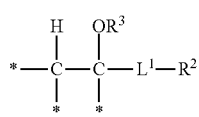

wherein, in the formulae (1-1) and (1-2),
$R^3$s each independently represent a hydrogen atom or an alkyl group having 1 to 8 carbon atoms; and
$L^1$, $R^2$ and * are as defined in the formula (1).

19. The production method according to claim 14, wherein a content of the compound in the composition is no less than 1% by mass and no greater than 50% by mass.

* * * * *